US008932619B2

(12) United States Patent
Ladet et al.

(10) Patent No.: US 8,932,619 B2
(45) Date of Patent: Jan. 13, 2015

(54) DURAL REPAIR MATERIAL

(75) Inventors: Sebastien Ladet, Lyons (FR); Philippe Gravagna, Irigny (FR); Yves Bayon, Lyons (FR)

(73) Assignee: Sofradim Production (FR)

( * ) Notice: Subject to any disclaimer, the term of this patent is extended or adjusted under 35 U.S.C. 154(b) by 770 days.

(21) Appl. No.: 11/823,275

(22) Filed: Jun. 27, 2007

(65) Prior Publication Data
US 2009/0004239 A1    Jan. 1, 2009

(51) Int. Cl.
*A61F 2/02*       (2006.01)
*A61L 27/34*     (2006.01)
*A61L 27/48*     (2006.01)
*A61L 27/56*     (2006.01)
*A61L 27/58*     (2006.01)
*A61L 31/10*     (2006.01)
*A61L 31/12*     (2006.01)
*A61L 31/14*     (2006.01)
*A61F 2/00*       (2006.01)

(52) U.S. Cl.
CPC . *A61F 2/02* (2013.01); *A61L 27/34* (2013.01); *A61L 27/48* (2013.01); *A61L 27/56* (2013.01); *A61L 27/58* (2013.01); *A61L 31/10* (2013.01); *A61L 31/129* (2013.01); *A61L 31/146* (2013.01); *A61L 31/148* (2013.01); *A61F 2/0063* (2013.01)
USPC .......................................................... 424/423

(58) Field of Classification Search
None
See application file for complete search history.

(56) References Cited

U.S. PATENT DOCUMENTS

| | | | |
|---|---|---|---|
| 4,400,833 A | 8/1983 | Kurland | |
| 4,511,653 A | 4/1985 | Play et al. | |
| 4,578,067 A * | 3/1986 | Cruz, Jr. | 602/50 |
| 4,931,546 A | 6/1990 | Tardy et al. | |
| 4,950,483 A | 8/1990 | Ksander et al. | |
| 4,970,298 A * | 11/1990 | Silver et al. | 530/356 |
| 5,201,764 A | 4/1993 | Kelman et al. | |
| 5,256,418 A | 10/1993 | Kemp et al. | |
| 5,263,983 A | 11/1993 | Yoshizato et al. | |
| 5,306,500 A | 4/1994 | Rhee et al. | |
| 5,328,955 A | 7/1994 | Rhee et al. | |
| 5,350,583 A | 9/1994 | Yoshizato et al. | |
| 5,376,375 A | 12/1994 | Rhee et al. | |
| 5,399,361 A | 3/1995 | Song et al. | |
| 5,413,791 A | 5/1995 | Rhee et al. | |
| 5,536,656 A | 7/1996 | Kemp et al. | |
| 5,565,210 A | 10/1996 | Rosenthal et al. | |
| 5,618,551 A | 4/1997 | Tardy et al. | |
| 5,681,568 A | 10/1997 | Goldin et al. | |
| 5,686,115 A | 11/1997 | Vournakis et al. | |
| 5,709,934 A | 1/1998 | Bell et al. | |
| 5,766,631 A | 6/1998 | Arnold | |
| 5,785,983 A | 7/1998 | Furlan et al. | |
| 5,800,541 A | 9/1998 | Rhee et al. | |
| 5,861,034 A | 1/1999 | Taira et al. | |
| 5,863,984 A | 1/1999 | Doillon et al. | |
| 5,871,767 A | 2/1999 | Dionne et al. | |
| 5,876,444 A | 3/1999 | Lai | |
| 5,891,558 A * | 4/1999 | Bell et al. | 428/218 |
| 5,962,136 A | 10/1999 | Dewez et al. | |
| 5,993,844 A | 11/1999 | Abraham et al. | |
| 5,997,895 A * | 12/1999 | Narotam et al. | 424/423 |
| 6,042,592 A * | 3/2000 | Schmitt | 606/151 |
| 6,083,522 A | 7/2000 | Chu et al. | |
| 6,165,488 A * | 12/2000 | Tardy et al. | 424/426 |
| 6,197,935 B1 | 3/2001 | Doillon et al. | |
| 6,221,109 B1 | 4/2001 | Geistlich et al. | |
| 6,264,702 B1 | 7/2001 | Ory et al. | |
| 6,312,474 B1 | 11/2001 | Francis et al. | |
| 6,391,333 B1 | 5/2002 | Li et al. | |
| 6,391,939 B2 | 5/2002 | Tayot et al. | |
| 6,410,044 B1 | 6/2002 | Chudzik et al. | |
| 6,440,167 B2 | 8/2002 | Shimizu | |
| 6,451,032 B1 * | 9/2002 | Ory et al. | 606/151 |
| 6,454,787 B1 | 9/2002 | Maddalo et al. | |
| 6,500,464 B2 | 12/2002 | Ceres et al. | |
| 6,509,031 B1 | 1/2003 | Miller et al. | |
| 6,514,286 B1 | 2/2003 | Leatherbury et al. | |
| 6,596,304 B1 | 7/2003 | Bayon et al. | |
| 6,599,323 B2 * | 7/2003 | Melican et al. | 623/23.72 |
| 6,599,524 B2 | 7/2003 | Li et al. | |
| 6,599,690 B1 | 7/2003 | Abraham et al. | |
| 6,652,594 B2 | 11/2003 | Francis et al. | |
| 6,656,488 B2 * | 12/2003 | Yi et al. | 424/423 |
| 6,682,760 B2 | 1/2004 | Noff et al. | |
| 6,706,684 B1 * | 3/2004 | Bayon et al. | 514/17.2 |
| 6,730,299 B1 | 5/2004 | Tayot et al. | |
| 6,743,435 B2 | 6/2004 | DeVore et al. | |
| 6,773,723 B1 | 8/2004 | Spiro et al. | |
| 6,790,454 B1 | 9/2004 | Abdul Malak et al. | |
| 6,893,653 B2 | 5/2005 | Abraham et al. | |
| 6,949,625 B2 | 9/2005 | Tayot | |

(Continued)

FOREIGN PATENT DOCUMENTS

EP    0 552 576 A1    7/1993
EP    0 625 891 B1    1/1997

(Continued)

OTHER PUBLICATIONS

Baxter Healthcare S.A., TISSUDURA Aug. 2004.*
The American Heritage® Dictionary of the English Language, Fourth Edition copyright ©2000 by Houghton Mifflin Company. Updated in 2003. Published by Houghton Mifflin Company.*
Matsumoto et al. "A Gelatin Coated Collagen-Polyglycolic Acid Composite Membrane as a Dural Substitute". ASAIO Journal 2001; 47 Pages 641-645.*
Laquerriere, J. Neurosurg., 78, 1993.*
Collins et al., Use of collagen film as a dural substitute: Preliminary animal studies, Journal of Biomaterials Research, vol. 25, pp. 267-276 (1991).
Laquerriere et al., "Experimental Evaluation of Bilayered Human Collagen as a Dural Substitute", Journal of Neurosurgery, American Association of Neurological Surgeons, vol. 78, No. 3, Jan. 1, 1993, pp. 487-491.

(Continued)

*Primary Examiner* — Aradhana Sasan
*Assistant Examiner* — Danah Al-Awadi

(57) ABSTRACT

Multilayer structures including a porous layer and a non-porous layer having a reinforcement member are useful as dural repair materials.

17 Claims, 1 Drawing Sheet

(56) References Cited

U.S. PATENT DOCUMENTS

| | | |
|---|---|---|
| 6,974,862 B2 | 12/2005 | Ringeisen et al. |
| 6,977,231 B1 | 12/2005 | Matsuda |
| 7,041,868 B2 | 5/2006 | Greene et al. |
| RE39,172 E * | 7/2006 | Bayon et al. ............... 424/444 |
| 7,098,315 B2 | 8/2006 | Schaufler |
| 7,175,852 B2 | 2/2007 | Simmoteit et al. |
| 7,192,604 B2 | 3/2007 | Brown et al. |
| 7,214,765 B2 | 5/2007 | Ringeisen et al. |
| 7,226,611 B2 | 6/2007 | Yura et al. |
| 2001/0008930 A1 | 7/2001 | Tayot et al. |
| 2003/0013989 A1 | 1/2003 | Obermiller et al. |
| 2003/0114937 A1 | 6/2003 | Leatherbury et al. |
| 2003/0133967 A1 | 7/2003 | Ruszczak et al. |
| 2003/0232746 A1 | 12/2003 | Lamberti et al. |
| 2004/0059356 A1 | 3/2004 | Gingras |
| 2004/0101546 A1 | 5/2004 | Gorman et al. |
| 2004/0215231 A1 | 10/2004 | Fortune et al. |
| 2005/0002893 A1 | 1/2005 | Goldmann |
| 2005/0123581 A1 * | 6/2005 | Ringeisen et al. ............ 424/423 |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2006/0094318 A1 | 5/2006 | Matsuda et al. |
| 2006/0135921 A1 | 6/2006 | Wiercinski et al. |
| 2006/0147501 A1 | 7/2006 | Hillas et al. |
| 2006/0167561 A1 | 7/2006 | Odar et al. |
| 2006/0216320 A1 | 9/2006 | Kitazono et al. |
| 2006/0252981 A1 | 11/2006 | Matsuda et al. |
| 2007/0031474 A1 | 2/2007 | Tayot |
| 2007/0161109 A1 | 7/2007 | Archibald et al. |
| 2007/0280990 A1 * | 12/2007 | Stopek .......................... 424/423 |
| 2009/0075382 A1 * | 3/2009 | Sachlos ........................ 435/398 |

FOREIGN PATENT DOCUMENTS

| | | | |
|---|---|---|---|
| EP | 0 943 346 | | 9/1999 |
| EP | 0 693 523 B1 | | 11/2002 |
| EP | 1 315 468 B1 | | 6/2005 |
| EP | 1 561 480 B1 | | 8/2005 |
| EP | 1 017 415 B1 | | 10/2005 |
| EP | 1 484 070 B1 | | 1/2006 |
| EP | 1 738 780 | | 1/2007 |
| EP | 1 782 848 A2 | | 5/2007 |
| FR | 2 715 405 | | 7/1995 |
| WO | WO 03/002168 | | 1/2003 |
| WO | WO 2004/078120 | | 9/2004 |
| WO | WO 2006023444 | * | 8/2005 |
| WO | WO 2005/112820 | | 12/2005 |
| WO | WO 2006/138098 | * | 5/2006 ............ A61K 38/39 |
| WO | WO 2006/138098 | | 12/2006 |
| WO | WO 2007/048099 A2 | | 4/2007 |
| WO | WO 2004/108179 | * | 6/2010 ............ A61L 27/24 |

OTHER PUBLICATIONS

Matsumoto et al., A Gelatin Coated Collagen-Polyglycol Acid Composite Membrane as a Dural Substitute Asaio Journal, Lippincott Williams & Wilkins/Asaio, Hagerstown, MD, US, vol. 47, No. 6, Nov. 1, 2001, pp. 641-645.

International Search Report from International Application No. PCT/IB2008/002706 dated Dec. 16, 2009.

* cited by examiner

DURAL REPAIR MATERIAL

TECHNICAL FIELD

Composite materials having a non-porous layer, a porous layer and a reinforcement member are useful as a patch for repair or partial replacement of dura mater.

DESCRIPTION OF THE RELATED ART

Dura mater refers to the membranes found between the skull and the brain and between the vertebral column and the spinal cord. Defects of the dura mater can produce a variety of undesirable consequences such as brain herniation, adhesion formation between the neural tissue and the overlying structures, pseudomeningocele, cortical scarring, cerebrospinal fluid fistulas and wound infection with potential propagation to the brain parenchyma.

Duraplasty is a plastic or reconstructive operation on the dura mater. Repair of a dural defect may require application of a dural substitute (commonly referred to as a dural patch), especially, for example, when a large defect is created in the dural envelope in the course of a surgical procedure (e.g., tumor removal) or as a result of trauma. Also, congenital anomalies such as Arnold Chiari malformation and myelomeningoceles and spinal dysraphic states may require a duraplasty as part of the repair.

There remains a need in the repair of dural defects for a material that can mimic the functionality characteristics of the dura mater and that possesses satisfactory handling characteristics.

SUMMARY

The present dural repair materials include a non-porous layer, a porous layer and a reinforcement member. In embodiments, the non-porous layer is a collagen containing film possessing anti-adhesion properties. In embodiments, the porous layer is a collagen containing foam that provides hemostatic properties. In embodiments, the reinforcement member is formed from fibers, such as, for example, monofilaments, multifilament braids, or staple fibers. In embodiments, the reinforcement member is a mesh.

Methods for producing the present dural repair materials are also described. In embodiments, a liquid solution based on a collagenic constituent destined to form the non-porous layer is cast on a substrate. The reinforcement member is applied to the solution, in embodiments becoming completely embedded therein by the application of additional solution on top of the original volume of solution. Prior to complete gelling, a pre-formed porous layer is laid on the surface of the gelling solution. Upon drying, the various components adhere to form a dural repair material.

DETAILED DESCRIPTION OF PREFERRED EMBODIMENTS

Figure 1:
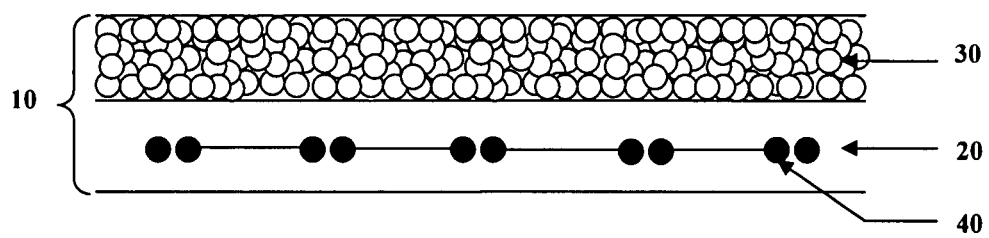
FIG. 1 is a schematic representation of a composite dural repair product in accordance with one embodiment of the present disclosure.

The present dural repair materials include at least a non-porous layer, a porous layer and a reinforcement member. As seen in FIG. 1, composite implant 10 includes non-porous layer 20, porous layer 30 and reinforcement members 40, which in this illustrative embodiment are embedded within non-porous layer 20. Each of these layers and processes for preparing each layer and the composite implant are described in greater detail below.

The Non-Porous Layer

The non-porous layer may retard or prevent tissue ingrowth from surrounding tissues thereby acting as an adhesion barrier and preventing the formation of unwanted scar tissue. Thus, in embodiments, the non-porous layer possesses anti-adhesion properties.

The non-porous layer of the present dural repair materials may be made from any bioabsorbable biocompatible natural or synthetic material. It should of course be understood that any combination of bioabsorbable materials may be used to form the non-porous layer.

Techniques for forming non-porous layers from such materials are within the purview of those skilled in the art and include, for example, casting, molding and the like.

Some non-limiting examples of bioabsorbable materials from which the non-porous layer may be made include but are not limited to poly(lactic acid), poly(glycolic acid), poly(hydroxybutyrate), polydioxanone, polyalkylene oxides, polyvinyl alcohols, polycaprolactone, poly(amino acids), polyalkylene oxalates, polyoxaesters, polyorthoesters, and copolymers, block copolymers, homopolymers, blends and combinations thereof.

In embodiments, natural biological polymers are used in forming the non-porous layer of the present dural repair materials. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, and combinations thereof. In addition, the natural biological polymers may be combined with any of the other polymeric materials described herein to produce the non-porous layer of the present dural repair materials.

In embodiments, an aqueous solution of a collagenic constituent is used to form the non-porous layer of the present dural repair materials. As used herein, the term "collagenic constituent" designates collagen which has at least partially lost its helical structure through heating or any other method, or gelatine. The term "gelatine" here includes commercial gelatine made of collagen which has been denatured by heating and in which the chains are at least partially hydrolyzed (molecular weight lower than 100 kDa). The collagenic constituent used may advantageously be formed of non-hydrolyzed collagen, mainly composed of α chains (molecular weight around 100 kDa). In the context of the present disclosure, α chains means complete α chains or fragments of these complete α chains produced by the loss of a small number of amino acids. The term "non-hydrolyzed" as used herein means that less than 10% of the collagenic chains have a molecular weight below about 100 kDa. If heating is used to denature the helical structure of the collagen, the heating should be moderate and provided under gentle conditions so as to avoid degradation by hydrolytic cleavage of the gelatine thus formed. Suitable gelatine materials are commercially available.

The collagen used can be of human or animal origin. It may particularly be type I porcine or bovine collagen, or type I or type III human collagen or mixtures in any proportions of the last two types. Native collagen may advantageously be used, in acid solution or after processing, to eliminate the telopeptides, notably by pepsin digestion. The collagen can also be modified by oxidative cleavage using any technique know to those skilled in the art, including, but not limited to the use of periodic acid or one of its salts as described by Tardy et al. in U.S. Pat. No. 4,931,546. Briefly, this technique involves mixing the collagen in acid solution with a solution of periodic acid or one of its salts at a concentration of between 1 and $10^{-5}$ M, in embodiments between $5\ 10^{-3}$ and $10^{-1}$ M, at a temperature of between 10 and 25° C. for 10 minutes to 72 hours. This process breaks down hydroxylysine and the sugars of the collagen, thus creating reactive sites without causing crosslinking. The oxidative cleavage of collagen allows moderate cross-linking later in the collagenic material. It should of course be understood that this function may be provided by other means of moderate cross-linking, for example by beta or gamma irradiation, or other agents of moderate cross-linking, for example chemical reagents at suitably low and non-toxic doses.

In embodiments, the non-porous layer of the composite material according to the present disclosure is made of collagen which is oxidized or a mixture in any proportions of non-oxidized and oxidized collagens.

In embodiments, a solution of collagenic constituent as defined above is used to form the non-porous layer. Typically, a collagen concentration from about 5 g/l to about 50 g/l, in embodiments from about 25 g/l to about 35 g/l is used.

The solution of oxidized collagen, non-oxidized collagen or a mixture thereof, thus prepared, may be heated, for example to a temperature in excess of 37° C., in embodiments to a temperature of between 40 and 50° C., for at least one hour. This results in at least partial denaturing of the collagen's helical structure. Other physical or chemical techniques for denaturing collagen (e.g., ultrasonication, or by the addition of chaotropic agents) are within the purview of those skilled in the art may also be used.

In embodiments, at least one macromolecular hydrophilic additive that is chemically unreactive with the collagenic constituent may be added to the solution used to form the non-porous layer. "Chemically unreactive with the collagenic constituent" as used herein means a hydrophilic compound which is not likely to react with the collagenic constituent, notably which does not form covalent bonds with it during cross-linking.

The macromolecular hydrophilic additive advantageously has a molecular weight in excess of 3,000 Daltons, in embodiments from about 3,000 to about 20,000 Daltons. Illustrative examples of suitable macromolecular hydrophilic additives include polyalkylene glycols (such as polyethylene glycol), polysaccharides (e.g., starch, dextran and/or cellulose), oxidized polysaccharides, and mucopolysaccharides. It should of course be understood that combinations of macromolecular hydrophilic additives may be used. The concentration of hydrophilic additive(s) can typically be from about 2 to about 10 times less than that of the collagenic constituent.

Typically, the macromolecular hydrophilic additive is eliminated by diffusion through the non-porous layer, in a few days. The swelling of this material may advantageously promote degradation of a collagenic non-porous layer in less than a month.

Optionally, glycerine may be added to the solution used to form the non-porous layer. When present, the concentration of glycerine in the solution can typically be from about 2 to about 10 times less than that of the collagenic constituent, in embodiments less than about one-third of the collagenic constituent concentration.

In illustrative embodiments of the solution used to form the non-porous layer, the concentrations of collagenic constituent, hydrophilic additive(s) and glycerine, when present, can be from about 2 to about 10% for the collagenic constituent, from about 0.6 to about 4% for the hydrophilic additive(s) and from about 0.3 to about 2.5% for glycerine, respectively.

The solution used to form the non-porous layer may be prepared by adding collagenic constituent, hydrophilic additive(s) and glycerine, when present, to water or a water/alcohol (e.g., ethanol) mixture at a temperature of 30 to 50° C. The solution may advantageously be neutralized to a neutral pH to avoid hydrolyzing the collagenic constituent by heating and to obtain a film of physiological pH while permitting pre-cross-linking of the collagenic constituent if the mixture contains oxidized collagen as indicated previously.

In embodiments, the non-porous layer is a collagen film made from either non heated oxidized collagen or heated oxidized collagen. The following table gives the concentration of illustrative collagen solutions that may be used to form the non-porous layer(s) of the present dural repair materials.

| | |
|---|---|
| Non heated oxidized collagen content | 0.1%-1% (w/w) |
| Heated Oxidized collagen content | 0.1%-6% (w/w) |

The Porous Layer

The porous layer of the present dural repair materials has openings or pores over at least a portion of a surface thereof. As described in more detail below, suitable materials for forming the porous layer include, but are not limited to foams (e.g., open or closed cell foams). In embodiments, the pores may be in sufficient number and size so as to interconnect across the entire thickness of the porous layer. In other embodiments, the pores do not interconnect across the entire thickness of the porous layer. Closed cell foams are illustrative examples of structures in which the pores may not interconnect across the entire thickness of the porous layer. In yet other embodiments, the pores do not extend across the entire thickness of the porous layer, but rather are present at a portion of the surface thereof. In embodiments, the openings or pores are located on a portion of the surface of the porous layer, with other portions of the porous layer having a non-porous texture. Those skilled in the art reading the present disclosure will envision other pore distribution patterns and configurations for the porous layer.

The porous layer of the present dural repair materials may be made from any bioabsorbable natural or synthetic material. It should of course be understood that any combination of bioabsorbable materials may be used to form the porous layer. Some non-limiting examples of materials from which the porous layer may be made include but are not limited to poly(lactic acid), poly(glycolic acid), poly(hydroxybutyrate), polydioxanone, polyalkylene oxides, polyvinyl alcohols, polycaprolactone, poly(amino acids), polyalkylene oxalates, polyoxaesters, polyorthoesters, and copolymers, block copolymers, homopolymers, blends and combinations thereof. In embodiments, natural biological polymers are used in forming the porous layer of the implant. Suitable natural biological polymers include, but are not limited to, collagen, gelatin, fibrin, fibrinogen, elastin, keratin, albumin, hydroxyethyl cellulose, cellulose, hydroxypropyl cellulose, carboxyethyl cellulose, and combinations thereof. Alternatively, the polymer constituent may be a polysaccharide, or polysaccharides modified by oxidation of alcohol functions into carboxylic functions such as oxidized cellulose. In addition, the natural biological polymers may be combined with any of the other polymeric materials described herein to produce the porous layer of the present dural repair materials.

Where the porous layer is a foam, the porous layer may be formed using any method suitable to forming a foam or sponge including, but not limited to the lyophilization or freeze-drying of a composition. Suitable techniques for making foams are within the purview of those skilled in the art.

The porous layer can be at least 0.1 cm thick, in embodiments from about 0.2 to about 1.5 cm thick. The porous layer can have a density of not more than about 75 mg collagen/cm$^2$ and, in embodiments below about 7 mg collagen/cm$^2$. The size of the pores in the porous layer can be from about 20 μm to about 300 μm, in embodiments from about 100 μm to about 200 μm.

In embodiments, the porous layer possesses haemostatic properties. Illustrative examples of materials which may be used in providing the porous layer with the capacity to assist in stopping bleeding or hemorrhage include, but are not limited to, poly(lactic acid), poly(glycolic acid), poly(hydroxybutyrate), poly(caprolactone), poly(dioxanone), polyalkyleneoxides, copoly(ether-esters), collagen, gelatin, thrombin, fibrin, fibrinogen, fibronectin, elastin, albumin, hemoglobin, ovalbumin, polysaccharides, hyaluronic acid, chondroitin sulfate, hydroxyethyl starch, hydroxyethyl cellulose, cellulose, oxidized cellulose, hydroxypropyl cellulose, carboxyethyl cellulose, agarose, maltose, maltodextrin, alginate, clotting factors, methacrylate, polyurethanes, cyanoacrylates, platelet agonists, vasoconstrictors, alum, calcium, RGD peptides, proteins, protamine sulfate, epsilon amino caproic acid, ferric sulfate, ferric subsulfates, ferric chloride, zinc, zinc chloride, aluminum chloride, aluminum sulfates, aluminum acetates, permanganates, tannins, bone wax, polyethylene glycols fucans and combinations thereof.

The haemostatic agents from which the porous layer can be made or which can be included in the porous layer can be in the form of foams, fibers, filaments, meshes, woven and nonwoven webs, compresses, pads, powders, flakes, particles and combinations thereof. For example, the implant may include commercially available types of hemostatic porous layers, such as materials based on oxidized cellulose (Surgicel® or Interceed®).

In embodiments, the porous layer is a made from non-denatured collagen or collagen which has at least partially lost its helical structure through heating or any other method, consisting mainly of non-hydrolyzed α chains, of molecular weight close to 100 kDa. The term "non-denatured collagen" means collagen which has not lost its helical structure. The collagen used for the porous layer of present implant may be native collagen or atelocollagen, notably as obtained through pepsin digestion and/or after moderate heating as defined previously. The collagen may have been previously chemically modified by oxidation, methylation, ethylation, succinylation or any other known process. The origin and type of collagen may be as indicated for the non-porous layer described above.

In embodiments, the porous layer can be obtained by freeze-drying an aqueous acid solution of collagen at a concentration of 2 to 50 g/l and an initial temperature of 4 to 25° C. The concentration of collagen in the solution can be from about 1 g/l to about 30 g/l, in embodiments about 10 g/l. This solution is advantageously neutralized to a pH of around 6 to 8.

The porous layer can also be obtained by freeze-drying a fluid foam prepared from a solution of collagen or heated collagen, emulsified in the presence of a volume of air in variable respective quantities (volume of air to water varying from about 1 to about 10).

In embodiments, a collagen sponge is obtained by freeze-drying a collagen suspension, resulting from the mixing of oxidized collagen and glutaraldehyde (GTA) cross-linked collagen, at different concentrations. Glutaraldehyde (GTA) cross-linked collagen is obtained by the incubation of a 1% neutralized collagen solution with a glutaraldehyde solution at a final concentration of 0.5%, at room temperature, during 1 hour. The suspension is then filtered and washed to remove the excess of GTA. Then, it is treated with sodium borohydride at room temperature until removal of the yellow coloration. The suspension is filtered, washed, and neutralized. The precipitate is washed several times, by acetone, to remove salts and water. The final precipitate is dried under vacuum or air flow, and stored at –20° C. Oxidized collagen is obtained by the oxidation of a 3% (w/w) collagen solution by periodic acid (C=8 mM) at room temperature, during 3 hours, in the manner described in Example 4 of U.S. Pat. No. 6,596,304, the entire disclosure of which is incorporated herein by this reference. The concentration of the two collagen types and the total amount of collagen in the suspension are detailed in the table below.

| | |
|---|---|
| (A) GTA cross-linked collagen content | 20%-100% (w/w total collagen) |
| (B) Oxidized collagen content | 80%-0% (w/w total collagen) |
| Total collagen concentration in the suspension | 0.2%-5% (w/w) |

The ratio (A/B) of concentration of the two collagen types may advantageously be between 1 and 5. The collagen sponge optionally can be then compacted by using a press, a calendar or any other appropriate means.

The Reinforcement Member

The present dural repair materials also include a reinforcement member. The reinforcement member may be positioned between the non-porous layer and the porous layer. Alternatively, the reinforcement member may be positioned entirely within the non-porous layer. It is also envisioned that the reinforcement member may be positioned at the surface of one of the layers making up the present multilayer dural repair materials and, in embodiments, may be positioned at an exterior surface of the present multilayer dural repair materials.

Some suitable non-limiting examples of the reinforcement member include fabrics, meshes, monofilaments, multifilament braids, chopped fibers (sometimes referred to in the art as staple fibers) and combinations thereof.

Where the reinforcement member is a mesh, it may be prepared using any technique known to those skilled in the art, such as knitting, weaving, tatting, knipling or the like. Illustrative examples of suitable meshes include any of those that are presently commercially available for hernia repair. In embodiments where a mesh is used as the reinforcement member, the mesh will aid in affixing the composite to tissue without tearing of the porous or non-porous layers.

Where monofilaments or multifilament braids are used as the reinforcement member, the monofilaments or multifilament braids may be oriented in any desired manner. For example, the monofilaments or multifilament braids may be randomly positioned with respect to each other within the present dural repair materials. As another example, the monofilaments or multifilament braids may be oriented in a common direction within the present dural repair materials. In embodiments, monofilaments or multifilament braids are associated with both the porous layer and with the non-porous layer. In an illustrative embodiment of this type, the present dural repair materials include a first reinforcement member having a plurality of reinforcement members oriented in a first direction within the non-porous layer and a second reinforcement layer having a plurality of reinforcement members oriented in a second direction within the porous layer. In embodiments, the first and second directions may be substantially perpendicular to each other.

Where chopped fibers are used as the reinforcement member, the chopped fibers may be oriented in any desired manner. For example, the chopped fibers may be randomly oriented or may be oriented in a common direction. The chopped fibers can thus form a non-woven material, such as a mat or a felt. The chopped fibers may be joined together (e.g., by heat fusing) or they may be unattached to each other. The chopped fibers may be of any suitable length. For example, the chopped may be from 0.1 mm to 100 mm in length, in embodiments, 0.4 mm to 50 mm in length. In an illustrative embodiment, the implant has randomly oriented chopped fibers that have not been previously fused together embedded within in the non-porous layer.

It is envisioned that the reinforcement member may be formed from any of the bioabsorbable, natural or synthetic materials previously described herein including derivatives, salts and combinations thereof. In embodiments, the reinforcement member is a surgical mesh made from polylactic acid fibers. Where monofilaments or multifilament braids are used as the reinforcement member, any commercially available bioabsorbable suture material may advantageously be employed as the reinforcement member.

In embodiments, the reinforcement member is a textile knitted with fully bioresorbable polylactic acid (PLA) threads designed to achieve suturability and reinforcement of the dural implant. The following table gives the technical data of illustrative PLA textiles that may be used as the reinforcement member in the present dural repair materials.

| | PLA textile technical data |
|---|---|
| Thread Multifilament | 84*/24° |
| Weight per surface (g/m²) | 20-40 |
| Pore sizes | 0.5-2 × 0.5-2 mm |
| Thickness | 0.2-0.4 mm |
| Filament diameter Multifilament | 18 µm |
| Cleaning procedure | Methanol-ether |
| Sterilization | γ rays |

*yarn count: 84 g for 10 000 m
°number of filaments

In other embodiments, a textile reinforcement member may be knitted by combining two different chemically fibers, such as PLA and oxidized cellulose.

In embodiments, the fibers of the reinforcement member may advantageously be coated by a biologic component so as to decrease the risk of inflammatory reaction and sepsis, particularly in already contaminated surgical sites. The solution used for the textile coating may be composed of any product which may limit the risk of inflammatory reaction and sepsis, such as, for example, oxidized collagen, glutaraldehyde cross-linked collagen, or polysaccharides (such as fucans). Advantageously, the fibers of the reinforcement member may be then processed by a surface treatment (for example, a plasma treatment with $N_2$) so as to impart hydrophilic properties and/or a positive charged at the surface of the reinforcement member. Such a treatment will facilitate coating of the reinforcement member, e.g., with collagen and/or polysaccharide solutions.

Optional Bioactive Agents

In some embodiments, at least one bioactive agent may be combined with the present dural repair materials and/or any of the individual components (the porous layer, the non-porous layer and/or the reinforcement member) used to construct the present dural repair materials. In these embodiments, the present dural repair material can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present dural repair materials in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive agents can be used to prevent adhesions from forming between the present dural repair materials and the surrounding tissues opposite the target tissue. In addition, anti-adhesive agents may be used to prevent adhesions from forming between the present dural repair materials and the packaging material. Some examples of these agents include, but are not limited to poly(vinyl pyrrolidone), carboxymethyl cellulose, hyaluronic acid, polyethylene oxide, poly vinyl alcohols and combinations thereof.

Suitable antimicrobial agents which may be included as a bioactive agent in the dural repair materials of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B and antimicrobial polysaccharides such as fucans and derivatives may be included as a bioactive agent in the dural repair materials of the present disclosure.

Other bioactive agents which may be included as a bioactive agent in the dural repair materials in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fingals; anti-virals; anticoagulants; anticonvulsants; antidepressants; antihistamines; and immunological agents.

Other examples of suitable bioactive agents which may be included in the present dural repair materials include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ((3-IFN, (a-IFN and y-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

Assembling the Composite

The multilayer dural repair materials described herein may be formed using any method known to those skilled in the art capable of connecting a non-porous layer to a porous layer. It is envisioned that the non-porous layer and the porous layer may be adhered to one another using chemical bonding, surgical adhesives, surgical sealants, and surgical glues. In addition, the layers may be bound together using mechanic means such as pins, rods, screws, clips, etc. Still further, the layers may naturally or through chemical or photoinitiation may interact and crosslink or provide covalent bonding between the layers.

Figure 2:
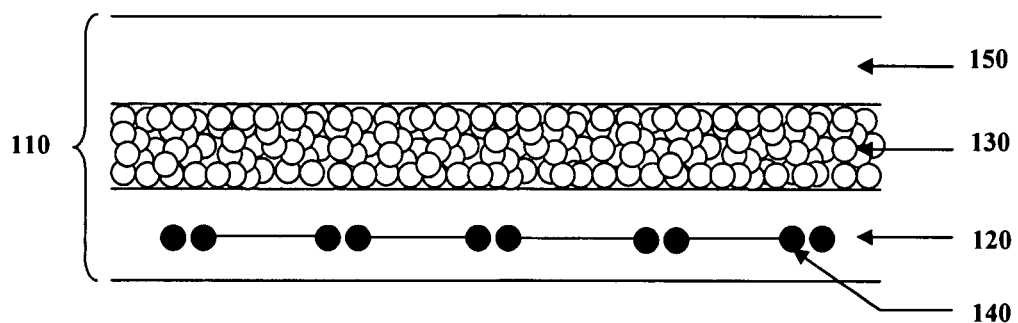
FIG. 2 is a schematic representation of a composite dural repair product in accordance with another embodiment of the present disclosure.

In the illustrative embodiment shown in FIG. 1, composite dural repair material 10 includes non-porous layer 20, porous layer 30 and reinforcement members 40, which are embedded within non-porous layer 20. In an alternative embodiment shown in FIG. 2, composite dural repair material 100 includes porous layer 130 sandwiched between reinforced non-porous layer 120, and a second non-porous layer 150. Those skilled in the art reading the present disclosure will readily envision other combinations of porous and non-porous layers suitable for use as dural repair materials.

In embodiments, the multilayer dural repair materials described herein are prepared by attaching the individual layers of materials together to form a multiple layer implant. The porous layer may be formed separate and apart from the non-porous layer. Alternatively, the porous and non-porous layers may be formed together.

In an illustrative embodiment, the present dural repair materials are prepared by first pouring a solution of collagenic constituent, destined to form the film, possibly containing the hydrophilic additive(s) and glycerine, onto an adequate, substantially flat support and distributing it evenly. The support is inert in that it does not react with the above-mentioned components and is not involved in the cross-linking process. The support may advantageously be made from a hydrophobic material such as, for example, PVC or polystyrene. However, this support can also consist of a strippable material which will remain slightly adhesive and which can then be separated from the implant at the time of surgical use. This support may itself also consist of a film, for example dried collagen, onto which the solution is poured, or a layer of collagenic material gel in a distinctly more advanced state of gelification.

The density of the thin layer initially applied as a solution to the substrate can be from about 0.1 g solution/cm$^2$ to about 0.3 g solution/cm$^2$. This collagenic solution advantageously may be poured at a temperature from about 4° C. to about 30° C., and in embodiments from about 18° C. to about 25° C. Once applied to the substrate, the collagen solution is allowed to partially gel. Partial gelling results from cooling of the collagen solution, and not from drying of the solution.

A mesh reinforcement member is then applied to the solution. Application of the reinforcement member onto the solution means simply laying the reinforcement member onto the solution or partially gelled solution, and optionally applying slight pressing. The pressing should be insufficient to cause any significant disruption of the portion of the layer of solution in contact with the substrate thereby helping to maintain the integrity and anti-adhesion characteristics of the non-porous layer. The pressing may leave the surface of the reinforcement member exposed at the surface of the solution or may embed the reinforcement member completely within the layer of solution.

Following application of the mesh reinforcement member, but before complete gellification of the initially applied solution, additional solution may be applied in an amount sufficient to cover the mesh, so that it is completely embedded within the solution. Where pressing has already embedded the reinforcement member in the solution, application of additional solution may be eliminated.

This solution containing the embedded mesh reinforcement member is left to gel and a porous layer prepared as indicated above is applied to the solution during gelification.

Application of the porous layer onto the solution during gelification means simply laying the porous layer onto the gel, and optionally applying slight pressing. The pressing should be insufficient to cause any significant compaction of the porous layer. In embodiments where the porous layer has been pre-formed, the porous layer will become joined to the solution, but will not become interlocked with the mesh reinforcement member.

The moment at which the porous layer is applied to the solution during gelification will depend upon the nature of the solution employed, the conditions under which the solution is maintained during gelification and the nature of the porous layer. Generally, the solution will allowed to gellify for a period of time prior to application of the porous layer such that the gel is still soft and allows the porous layer to penetrate over a distance which is advantageously from about 0.05 mm to about 2 mm and, in embodiments from about around 0.1 mm to about 0.5 mm. The appropriate moment for application of the porous layer for any given combination of materials/conditions can be determined empirically, for example by applying small samples of the porous layer to the gel at various times and evaluating the degree of penetration and adherence. Generally, when the solution which is gelling is at a temperature of between 4 and 30° C., the porous layer can be applied 5 to 30 minutes after the solution has been poured over the surface holding it.

The composite implant is left to dry or dried in order to obtain the final implant. When the collagenic solution destined to form the film includes oxidized collagen, it is polymerized while the material is drying. This drying occurs favorably at a temperature of from about 4° C. to about 30° C., in embodiments from about 18° C. to about 25° C. The material can be dried in a jet of sterile air if desired.

After drying, the implant can be separated from its support, packaged and sterilized using conventional techniques, e.g., irradiation with beta (electronic irradiation) or gamma (irradiation using radioactive cobalt) rays. In embodiments where hydrolytically unstable materials are used in forming the composite, such as polyglycolic acid, polylactic acid the composites are packaged under sufficiently dry conditions to ensure that no degradation of the composite takes place during storage.

The present dural repair materials are stable at ambient temperature and remains stable for long enough to be handled at temperatures which may rise to 37-40° C. The thickness of the non-porous layer is not critical, but typically can be less than about 100 μm thick, and in embodiments from about 30 μm to about 75 μm thick. Likewise, the thickness of the porous layer is not critical, but typically can be from about 0.1 mm to about 1.4 mm thick. The overall thickness of the dural repair material is not critical, but typically can be from about 0.2 mm to about 1.5 mm thick, and in embodiments from about 0.3 mm to about 0.8 mm thick. The dural repair materials in accordance with this disclosure can be produced at a desired size or produced in large sheets and cut to sizes appropriate for the envisaged application.

The present dural repair materials may be implanted using open surgery or in a laparoscopic procedure. When implanted laparoscopically, the present dural repair materials should be rolled with the porous side on the inside before trocar insertion.

The following non-limiting example illustrates the preparation of dural repair materials in accordance with the present disclosure.

EXAMPLES

Preparation of Textile Reinforcement Member Coated with Oxidized Collagen

Oxidized collagen is obtained by the oxidation of a 3% collagen solution by periodic acid, at a final concentration of 8 mM, at room temperature, during 3 hours as described in Example 4 of U.S. Pat. No. 6,596,304. To a 3% oxidized collagen solution, a sterile concentrated solution of PEG 4000 (polyethylene glycol having a molecular weight of 4000 g/mol) and glycerol, in order to achieve a PEG concentration of 1% and a glycerol concentration of 0.6%. The pH of the solution is adjusted to 7.0 by adding concentrate sodium hydroxide solution. The volume of the solution is then adjusted with sterile water to obtain final concentrations of collagen, PEG and glycerol of 2.7%, 0.9% and 0.54% respectively. The textile is soaked once or twice into the oxidized collagen solution, then dried, so as to cover as much as possible the overall accessible surface of PLA fibres of the 2D textile.

Preparation of Textile Reinforcement Member Coated with GTA Cross-linked Collagen The textile is coated with GTA cross-linked collagen, in two steps. It is first soaked once or twice into a collagen solution (1% w/w) and then dried. Then, the coated textile is cross-linked in a solution of glutaraldehyde with a concentration of 0.5% for 1 hour. It is further treated with sodium borohydride during at least two hours, until the initial yellowish appearance of fibers was completely removed to give white fibers. The textile is then washed several times in sterile water and finally dried.

Preparation of Textile Reinforcement Member Coated with GTA Cross-linked Collagen The textile is coated with GTA cross-linked collagen, in two steps. It is first sprayed with a collagen solution (1% w/w), several times up to ten times. After each series of spraying, the collagen laid on the mesh is completely dried in an oven, at +50° C. Then, the coated textile is cross-linked in a solution of glutaraldehyde with a concentration of 0.5% for 1 hour. It is further treated with sodium borohydride during at least two hours, until the initial yellowish appearance of fibers was completely removed to give white fibers. The textile is then washed several times in sterile water and finally dried.

Preparation of Calendered Collagen Porous Layer

A collagen suspension is obtained by mixing GTA cross-linked collagen and oxidized collagen in relative concentrations of 80%/20% respectively. The total collagen concentration in the aqueous solution is fixed at 1.5% w/w. Then, the suspension is poured in Petri dishes and freeze-dried. Finally the collagen sponges are calendered to obtain a maximal thickness of 0.15 mm.

Preparation of Oxidized Collagen Solution/suspension

To a 3.9% oxidized collagen solution, an ultra-filtered concentrated solution of PEG 4000 (polyethylene glycol having a molecular weight of 4000 g/mol) and glycerol is added, in order to achieve a PEG concentration of 1% and a glycerol concentration of 0.6%. The pH of the solution is adjusted to 7.0 by adding concentrate sodium hydroxide solution. The volume of the solution is then adjusted with sterile water to obtain final concentrations of collagen, PEG and glycerol of 2.7%, 0.9% and 0.54%, respectively.

Preparation of the Oxidized Collagen Solution/suspension

To a 3.9% oxidized collagen solution, an ultra-filtered concentrated solution of PEG 4000 (polyethylene glycol having a molecular weight of 4000 g/mol) and glycerol is added, in order to achieve a PEG concentration of 1% and a glycerol concentration of 0.6%. To the solution is added one part of dry GTA cross-linked collagen for 5 parts of oxidized collagen by weight. The pH of the suspension is adjusted to 7.0 by adding concentrate sodium hydroxide solution. The volume of the solution is then adjusted with sterile water to obtain final concentrations of collagen, GTA cross-linked collagen, PEG and glycerol of 2.7%, 0.55%, 0.9% and 0.54%, respectively.

Preparation of the Oxidized Collagen Solution/suspension

To a 3.9% oxidized collagen solution, an ultra-filtered concentrated solution of PEG 4000 (polyethylene glycol having a molecular weight of 4000 g/mol) and glycerol is added, in order to achieve a PEG concentration of 1% and a glycerol concentration of 0.6%. To the solution is added one part of dry GTA cross-linked collagen for 20 parts of oxidized collagen by weight. The pH of the suspension is adjusted to 7.0 by adding concentrate sodium hydroxide solution. The volume of the solution is then adjusted with sterile water to obtain final concentrations of collagen, GTA cross-linked collagen, PEG and glycerol of 2.7%, 0.13%, 0.9% and 0.54%, respectively.

Assembly of a Two-layer Dural Implant

An oxidized collagen solution is poured in a thin layer on a flat hydrophobic support of the PVC or polystyrene type, with a density of 0.266 g solution/cm$^2$, then a coated mesh is laid over the collagen solution, pressed into the solution and the application of additional solution on top of the original volume of solution. The surfaces are then exposed to a sterile stream of air at ambient temperature, during less than half of an hour. A calendered sponge is then gently applied on the gelling layer of oxidized collagen and the two layers are exposed to a sterile stream of air at ambient temperature. The two layers composite is exposed to a sterile stream of air at ambient temperature, leading to complete evaporation in at least approximately 18 hours.

Assembly of a Three-layer Dural Implant

An oxidized collagen solution is poured in a thin layer on a flat hydrophobic support of the PVC or polystyrene type, with a density of 0.400 g solution/cm², and then a textile reinforcement member is laid over the collagen solution, pressed into the solution and the application of additional solution on top of the original volume of solution. The surfaces are then exposed to a sterile stream of air at ambient temperature, during less than one hour. A calendered sponge is then gently applied on the gelling layer of oxidized collagen and the two layers are exposed to a sterile stream of air at ambient temperature, overnight. At this step, a second layer of oxidized collagen solution is distributed on the bi-layer composite with a reduced density, 0.133 g solution/cm². The three layers composite is exposed to a sterile stream of air at ambient temperature, leading to complete evaporation in at least approximately 18 hours.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

What is claimed is:

1. A dural repair material comprising a foam layer comprising a mixture of oxidized collagen and glutaraldehyde crosslinked collagen joined to a non-porous film comprising crosslinked, oxidized collagen, and a mesh reinforcement member embedded within the non-porous film, wherein the mixture comprises a ratio of concentration of the oxidized collagen and glutaraldehyde crosslinked collagen between 1:1 and 1:5.

2. A dural repair material comprising a porous layer comprising a mixture of oxidized collagen and glutaraldehyde crosslinked collagen joined to a non-porous layer comprising crosslinked, oxidized collagen and containing at least one mesh reinforcement member embedded within the non-porous layer, wherein the mixture comprises a ratio of concentration of the oxidized collagen and glutaraldehyde crosslinked collagen between 1:1 and 1:5.

3. A dural repair material comprising a porous layer comprising a mixture of oxidized collagen and glutaraldehyde crosslinked collagen sandwiched between a mesh reinforced non-porous layer comprising crosslinked, oxidized collagen and a second non-porous layer comprising a collagenic constituent, wherein the mixture comprises a ratio of concentration of the oxidized collagen and glutaraldehyde crosslinked collagen between 1:1 and 1:5.

4. The dural repair material of any of claims 1, 2 or 3 further comprising a bioactive agent.

5. The dural repair material of claim 1, wherein the mesh reinforcement member is produced from a bioabsorbable material.

6. The dural repair material of claim 1, wherein the non-porous layer comprises 0.1% to 1% (w/w) of non-heated oxidized collagen.

7. The dural repair material of claim 1, wherein the non-porous layer comprises 0.1% to 6% (w/w) of heated oxidized collagen.

8. The dural repair material of claim 2, wherein the mesh reinforcement member is produced from a bioabsorbable material.

9. The dural repair material of claim 2, wherein the non-porous layer comprises 0.1% to 1% (w/w) of non-heated oxidized collagen.

10. The dural repair material of claim 2, wherein the non-porous layer comprises 0.1% to 6% (w/w) of heated oxidized collagen.

11. The dural repair material of claim 3, wherein the mesh reinforcement member is produced from a bioabsorbable material.

12. The dural repair material of claim 3, wherein the mesh reinforced non-porous layer comprises 0.1% to 1% (w/w) of non-heated oxidized collagen.

13. The dural repair material of claim 3, wherein the mesh reinforced non-porous layer comprises 0.1% to 6% (w/w) of heated oxidized collagen.

14. The dural repair material of claim 3, wherein the second non-porous layer is formed from a mixture of oxidized collagen and glutaraldehyde crosslinked collagen.

15. The dural repair material of claim 1, wherein the foam layer is calendared.

16. The dural repair material of claim 2, wherein the porous layer is calendered.

17. The dural repair material of claim 3, wherein the porous layer is calendered.

* * * * *